United States Patent [19]

Maurer

[11] Patent Number: 4,670,580

[45] Date of Patent: Jun. 2, 1987

[54] PROCESS FOR PREPARING OLIGOMERIC GLYCOL ESTERS OF DICARBOXYLIC ACIDS

[75] Inventor: Charles J. Maurer, Matthews, N.C.

[73] Assignee: Celanese Corporation, New York, N.Y.

[21] Appl. No.: 845,911

[22] Filed: Mar. 31, 1986

[51] Int. Cl.$^4$ .............................................. C07C 67/08
[52] U.S. Cl. ......................................... 560/89; 560/91; 560/94; 560/198; 560/204
[58] Field of Search ...................... 560/89, 91, 94, 198

[56] References Cited

U.S. PATENT DOCUMENTS 3,551,386 12/1970 Berkau et al. .................... 560/89 X
4,018,815 4/1977 Vogt et al. ........................ 560/91 X Primary Examiner—Natalie Trousof
Assistant Examiner—Vera C. Clarke
Attorney, Agent, or Firm—Forrest D. Stine

[57] ABSTRACT

The invention provides a process for the preparation of a polyester oligomer capable of being further polymerized to a high polymer wherein a glycol-dicarboxylic acid ester feed is treated in a secondary esterification zone under conditions such that the partial vapor pressures of water and glycol are maintained at a cumulative level of less than 740 Torr, with water and glycol vapors being continuously removed from the secondary esterification zone, and free glycol being added to the secondary esterification zone in an amount sufficient to maintain a stable amount of liquid glycol in the secondary esterification zone. In various preferred embodiments of the invention, the secondary esterification zone can be maintained at a pressure substantially below atmospheric and the vapors from secondary esterification can be passed to a reflux column wherein glycol is condensed and returned to the secondary esterification zone, or the secondary esterification can be maintained at a pressure of about atmospheric and an inert gas can be injected into the vapor space thereby lowering the partial vapor pressures of water and glycol.

10 Claims, 2 Drawing Figures

PROCESS FOR PREPARING OLIGOMERIC GLYCOL ESTERS OF DICARBOXYLIC ACIDS

BACKGROUND OF THE INVENTION

1. Field of the Invention

This invention relates to an improved process for the production of oligomeric glycol esters of dicarboxylic acids, as exemplified by the production of an oligomeric ethylene glycol ester of terephthalic acid. This oligomer or prepolymer is then used to prepare a high molecular weight polyethylene terephthalate composition suitable for fabrication into films, tapes and fibers.

2. The Prior Art

Synthetic linear polyesters of fiber-forming molecular weight, such as polyesters of aromatic dicarboxylic acids, are prepared by processes involving an esterification step or steps, followed by a polymerization step or steps. Esterification is conducted by reacting dicarboxylic acid with a glycol (direct esterification) or by esterifying the aromatic dicarboxylic acid with a monohydric alcohol such as methyl alcohol and then transesterifying the resulting diester of the acid with a glycol (transesterification). For example, in the transesterification process, the dimethyl ester of terephthalic acid is heated with ethylene glycol in the presence of a transesterification catalyst to produce the bis-glycol ester of terephthalic acid, methyl alcohol and excess ethylene glycol being distilled off. This product is then polymerized by a condensation reaction with the elimination of ethylene glycol by heating the product at elevated temperatures under reduced pressures until a high molecular weight product is formed.

In the direct esterification process, a dicarboxylic acid, e.g., terephthalic acid, is condensed with glycol, e.g., ethylene glycol, to form the ester reaction product. The low molecular weight prepolymer or oligomer is then polymerized by heating under reduced pressures to form a high molecular weight polyester product.

Direct esterification is typically conducted in two steps, primary esterification followed by secondary esterification. In the primary esterification stage, dicarboxylic acid, e.g., terephthalic acid, is reacted with a molar excess of glycol, e.g., ethylene glycol to provide a glycol ester having a chain length or degree of polymerization greater than 1, e.g., 2-3, and a degree of esterification such that at least 70 mole percent, typically 85 mole percent or more, of carboxyl end groups are esterified. Typical operating conditions for the primary esterification stage include temperatures ranging from 220° C. to 280° C. and atmospheric or super-atmospheric pressures.

In the secondary esterification stage, the product of primary esterification is reacted, typically at a temperature of between 250° C. to 280° C., and which is higher than the primary esterification temperature, and at atmospheric pressure or super-atmospheric pressure for a time sufficient to increase the degree of polymerization to between about 4 and about 6. The resultant oligomer must have a substantial excess of hydroxyl end groups in order to be capable of further polymerization into a polymer, see for example, U.S. Pat. No. 3,551,386 to Berkau et al. Thus the oligomers typically will have carboxyl end group concentration (CEG) of from about 200 to about 350 microequivalents per gram ($\mu$eq/g).

The oligomeric product of secondary esterification is then polymerized in a low polymerization stage characterized by sub-atmospheric pressure in the range of from 10 to 50 Torr and at a temperature of from 270° C. to 290° C., followed by further polymerization in a final stage at sub-atmospheric pressure of from about 0.5 to 2.5 Torr and a temperature of up to about 300° C. An intermediate polymerization step between the low and high polymerization step may also be employed.

The art has found a correlation of strength retention and hydrolytic stability with a low CEG level in synthetic linear polyesters such as polyethylene terephthalate when fibers manufactured from the polyester are exposed to high temperature operating conditions as when such fibers are used in industrial end uses, such as for reinforcing cords on fabrics in rubber articles including pneumatic tires which operate at high temperatures caused by high speeds and heavy loads.

In prior art processes, in order to minimize the CEG level in the final polymer, such as polyethylene terephthalate, the secondary esterification step or stage is typically conducted at a relatively high ethylene glycol/terephthalic acid (EG/TA) mole ratio (MR), e.g., in the order of 1.30 to 1.50/1, in order to provide fewer unreacted carboxyl end groups in the oligomer. But the use of this high mole ratio results in the formation of glycol dimer, e.g., diethylene glycol, (DEG) which is incorporated in the polymer chain and has the effect of reducing the thermal and light stability of fibers and films prepared therefrom which is undesirable in industrial fibers. The presence of glycol dimer in the polymer product also lowers the softening point of the polymer. The lowering of the softening point is likewise undesirable in industrial fibers. Similarly, glycol dimer may be undesirable in textile fibers for various reasons.

Furthermore, excess ethylene glycol which is present in the oligomer and is not removed during the oligomerization reaction must be removed in the downstream final polymerization, which increases the cost of the polymerization reaction. The molar amount of the glycol such as ethylene glycol can be reduced, i.e., to an EG/TA mole ratio of 1.2:1 or lower. But this can result in a decrease in the degree of esterification with the undesirable result of passing unreacted terephthalic acid into the low polymerizer and a decrease in oligomer degree of polymerization unless primary esterifier temperature is increased, which, in turn results in increased DEG.

Thus, with respect to the present state of the art of preparing synthetic linear polyesters such as polyethylene terephthalate, the CEG level of the polymer can be reduced but only at the expense of increased DEG, a lower oligomer DP and/or the use of substantial excesses of glycol.

It is an object of this invention to provide an improved process for reducing either or both of the CEG and glycol dimer, e.g., DEG, concentration in synthetic linear polyesters. A further object of this invention is to provide a process whereby synthetic linear polyesters are obtained having CEG and/or DEG levels lower than has heretofore been possible in a conventional polymerization process. Still further objects of the invention include the provisions of a secondary esterification process stage which can provide an oligomer having an increased degree of polymerization and containing a deceased content of free glycol. Other objects of the invention will become apparent from a full reading and consideration of the following specification.

SUMMARY OF THE INVENTION

The invention provides an improved process for the preparation of a polyester oligomer capable of being further polymerized to form a polyester of fiber-forming molecular weight. Surprisingly it has been found that the esterification equilibrium can be forced towards a prepolymer having a higher degree of polymerization in a stable secondary esterification reaction which involves milder operating conditions than the prior art as follows. A glycol-dicarboxylic acid ester feed having an average degree of polymerization greater than 1 and having less than 30 mole percent free acid end groups is treated in a secondary esterification stage at a temperature of between about 200° C. and about 300° C. and a pressure of between 100 Torr and atmospheric pressure to further esterify the feed and liberate water and glycol and water vapors. The partial vapor pressures of water and glycol are maintained at a cumulative level of less than 740 Torr. Water and glycol vapors are continuously removed during the secondary esterification stage. Free glycol is added during the secondary esterification stage in an amount sufficient to maintain a liquid phase of glycol. The resultant oligomeric product exhibits one or more improved properties including an increased degree of polymerization, lower CEG content, lower DEG content and/or lower free glycol content.

It has been found that by maintaining the sum of partial pressures of glycol and water vapors below 740 Torr, the reaction equilibrium is forced towards a higher oligomer chain length. This can be accomplished by simply reducing the pressure during the secondary esterification stage to sub-atmospheric pressure or by operating at or about atmospheric pressure while introducing an inert gas such as nitrogen into the overhead vapor space of the secondary esterification zone in an amount sufficient to substantially reduce the partial vapor pressure of water and of glycol.

Surprisingly it has been found that liquid/vapor equilibrium can be maintained between liquid and vapor phase glycol even at temperatures which are greater than the boiling point of the glycol at the sub-atmospheric pressures used in the process of the invention. To obtain this vapor/liquid phase glycol equilibrium, liquid glycol is added to the secondary esterification zone at a rate sufficient to replace glycol vapor lost as a result of the reduced pressures. Glycol can be added to the secondary esterification stage by means of a reflux distillation column operating under a vacuum which separates water from the glycol and returns the glycol to the secondary esterification stage, or by introducing excess glycol into the secondary esterification zone, for example, as a component of the feed.

As will hereinafter be more fully demonstrated, the oligomers obtained in accordance with the practice of the present invention have unexpectedly low CEG and glycol dimer concentration levels, and the polymers obtained therefrom have similarly reduced CEG and dimer levels.

In preferred embodiments of the invention, a glycol/acid feed to the esterification process having a mole ratio of 1.3 or less, preferably 1.2 or less, is used. As the conditions used for oligomerization are relatively mild, e.g., sub-atmospheric pressures and relatively moderate temperatures, e.g., 250° C.-270° C., and excess glycol needed for esterification is reduced, the formation of dimer products is minimized. The oligomer prepared in accordance with the process of the present invention has a greater degree of polymerization and a substantially lower CEG content compared to oligomers prepared by prior art processes wherein the same mole ratios and temperatures are used. The oligomers represent highly reactive prepolymers which ultimately provide a low CEG level in the final polymer. Since the reactivity of the oligomer of the present invention is high, less severe reaction conditions can be used in the polymerization zone which in turn results in a lesser DEG formation due to polymer degradation. Finally, as the glycol/acid molar ratios required for the esterification reactions are relatively low, a comparatively lower amount of excess glycol is present in the oligomer with the result that the cost and complexity of the polymerization conditions can be greatly reduced.

DETAILED DESCRIPTION OF THE INVENTION

Figure 1:
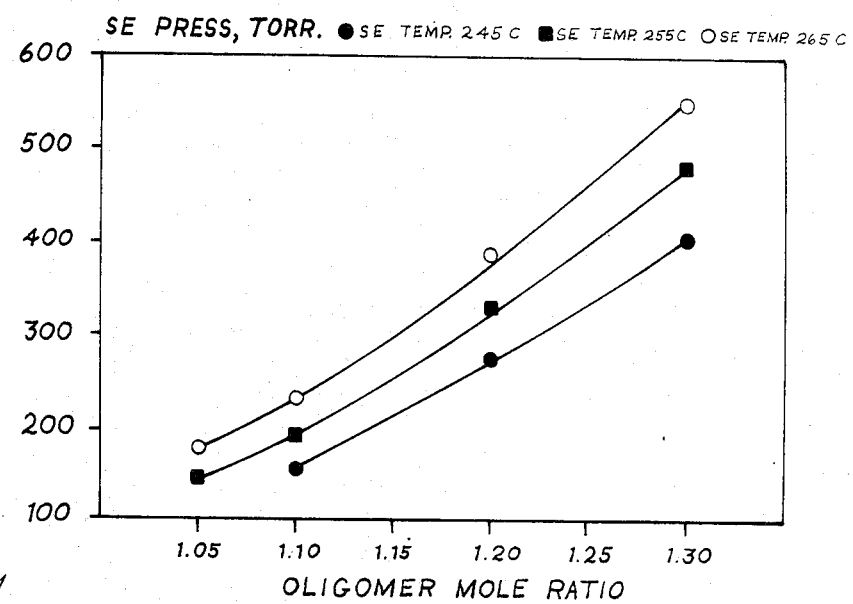

The invention is illustrated by means of embodiments utilizing the reaction of terephthalic acid with ethylene glycol. But it is to be understood that the invention is related generally to the esterification of a dicarboxylic acid with a glycol.

Polyesters which may be prepared in accordance with the process of the present invention are those resulting from reacting a glycol of the series $HO(CH_2)_nOH$, in which n is an integer from 2 to 10, with one or more dicarboxylic acids. Among the dicarboxylic acids useful in the present invention are terephthalic acid, isophthalic acid, sebacic acid, adipic acid, succinic acid, p,p'-dicarboxybiphenyl, p,p'-dicarboxydiphenylpropane, p,p'-dicarboxydiphenylbutane, oxalic acid, glutaric acid, pimelic acid, suberic acid, and azelaic acid. Examples of the glycols which may be used to prepare synthetic linear polyesters in accordance with the present inventions are ethylene glycol, trimethylene glycol, tetramethylene glycol, decamethylene glycol and the like. Polyethylene terephthalate, however, is preferred because of the ready availability of terephthalic acid and ethylene glycol, from which it is made. It also has a relatively high melting point (cross filament fusion) of about 250° C. through 265° C. and this property is particularly desirable in the manufacture of filaments in the textile industry.

The feed for the secondary esterification stage process of the present invention contains a glycol ester of a dicarboxylic acid such as terephthalic acid which is prepared in a primary esterification zone. The glycol ester feed can be prepared by direct esterification between the glycol and the dicarboxylic acid. The molar ratio of glycol to dicarboxylic acid used to prepare the glycol ester is advantageously between about 1.3/1 and 1.01/1, preferably 1.25/1 or less, more preferably 1.2/1 or less. Where very low levels of CEG in the final polymer is not a requirement, mole ratios of 1.1/1 and even 1.05/1 or less can be used. The preparation of the glycol ester reaction product of the primary esterification stage requires esterification of more than 70 mole percent of dicarboxylic acid end groups, preferably at least 85 mole percent of acid end groups are esterified. Primary esterification is normally conducted by reacting the acid and glycol at super-atmospheric pressures, e.g., at about 5 to about 50 psig and preferably about 10 to about 40 psig, at temperatures of about 220° C. to about 275° C., and preferably about 245° C. to about 270° C. and for residence times in the range of 1 to 6 hours. Further, primary esterification is conducted to obtain a degree of polymerization of greater than 1, preferably between about 2.0 and 4.0. Degree of polymerization may conveniently be determined by measuring the relative viscosity of an 8% solution in orthochlorophenol. Mole percent unreacted acid end groups may conveniently be determined by titrating an orthocresol solution of the polymer with 0.1 N NaOH.

The oligomerization or secondary esterification stage of this invention is conducted by heating the glycol ester reaction product to a temperature between about 200° C. and about 300° C., temperatures between about 240° C. and about 275° C. being preferred. The primary and secondary esterification stages can be conducted in the same vessel or different vessels. Additionally, the secondary esterification stage can be conducted in a single vessel or in a series of vessels. The temperature used in the oligomerization or secondary esterification reaction can be above the boiling point of the glycol used at the pressures employed for the reaction. Residence times in the secondary esterification stage can range from ¼ to 6 hours.

It is a critical factor in the practice of the invention that the sum of partial vapor pressures of water and glycol during the secondary esterification stage be maintained at less than 740 Torr. This drives the esterification reaction equilibrium towards a higher degree of oligomerization with a concomitant lowering of the CEG level. To achieve this according to one embodiment of the invention a sub-atmospheric pressure of between about 100 Torr and 740 Torr is maintained during the secondary esterification stage. Preferably, pressure is maintained between about 100 and about 650 Torr, or even more preferably, between about 150 and about 450 Torr. It will be recognized that the pressure, temperature and residence time employed during the secondary esterification stage will be dependent on the glycol/dicarboxylic acid mole ratio, desired CEG content and desired chain length of the final oligomer, as discussed more fully hereinafter.

According to another embodiment of the invention, the cumulative partial vapor pressures of glycol and water are reduced by adding or injecting an inert gas such as nitrogen into the secondary esterification zone or vessel vapor space. In this embodiment, secondary esterification can be conducted at or near atmospheric pressure but the addition of nitrogen causes a reduction in the partial vapor pressure of water. The nitrogen is added to the secondary esterification zone at a rate or in an amount sufficient to reduce the sum of partial pressures of glycol and water to below 740 Torr, preferably to between about 200 and 650 Torr and more preferably to between about 200 and 450 Torr. Since the vapor in the secondary esterification zone will, in this embodiment of the invention, consist essentially of the three components, inert gas, glycol vapor and steam; the partial pressures of the vapors can readily be calculated from the total pressure of the secondary esterification zone and the molar percentages of the three main components of the vapor space, as readily determined by analysis.

Inert gas added to the vapor space should be added in a manner to assure substantially even distribution throughout the vapor space. Additionally, it is desirable to preheat the gas to a temperature at or near that of the secondary esterification stage to avoid causing condensation in the vapor space. Regardless of whether secondary esterification is conducted at sub-atmospheric pressure or whether inert gas is used to reduce the partial vapor pressure of water, ethylene glycol and water vapors will be removed in the overhead. But it is necessary that liquid glycol be present in the secondary esterification zone in order to produce prepolymers having low CEG content and which are capable of further polymerization to form a high polymer, i.e., of fiber forming molecular weight.

It is a second critical factor of the invention that glycol be added to the secondary esterification zone in an amount sufficient to maintain liquid glycol, i.e., unreacted glycol in the liquid state, so that a liquid vapor equilibrium is established in the secondary esterification zone. The amount of liquid glycol in the secondary esterification zone should not exceed about 30 mole percent based on acid, both reacted and unreacted, e.g., moles terephthalate and terephthalic acid. Preferably the liquid glycol should not exceed 20 mole percent, more preferably should not exceed 5 percent.

In one advantageous embodiment of the invention, glycol is added by separating and returning all or a portion of the glycol liberated from the secondary esterification zone. To accomplish this, the water vapor released during the secondary esterification reaction together with any glycol vapor liberated during the reaction is passed to a distillation means, such as a reflux condenser or fractionating column where the glycol is condensed and returned to the secondary esterification zone. Water vapor is separated from the condensed glycol and vented from the system before the glycol is recycled to the secondary esterification zone.

Alternatively, or in combination with partial or total glycol reflux, all or a portion of glycol added to the secondary esterifier may be added as a component of the feed. Thus for example, if it is desired to maintain an EG/TA mole ratio of 1.10 in a continuous secondary esterification zone operating under a sub-atmospheric pressure, the feed can have an EG/TA mole ratio of 1.10 and liquid glycol can be maintained in the esterification zone by passing the overhead through a reflux column which separates and returns all glycol vapor to the esterification zone. But, alternatively, a 1.20 mole ratio feed can be passed into the primary esterifier thereby preparing a 1.20 mole ratio feed to the secondary esterifier which in turn is then operated at a sub-atmospheric pressure sufficient to continuously remove glycol from the secondary esterifier at a rate to maintain a 1.10 mole ratio reaction mixture in the secondary esterification zone.

For any given mole ratio reaction mixture and reaction temperature, there will be a minimum pressure below which the secondary esterification zone cannot be operated without decreasing the glycol/acid mole ratio. This is defined by the partial vapor pressure of glycol at the desired temperature and mole ratio in the reaction mixture. The minimum pressure can also be determined experimentally by operating secondary esterification with sufficient reflux to return all glycol to the vessel while decreasing pressure. As pressure is decreased, a minimum pressure will be reached at which the maximum possible reflux, i.e., 100 percent reflux, will be required in order not to lose glycol vapor from the reflux. Below this pressure, at the given temperature, secondary esterification can only be operated at a lower mole ratio reaction mixture.

FIG. 1 illustrates the approximate minimum operating pressures for secondary esterification as a function of EG/TA mole ratio in the secondary esterification zone at temperatures of 245° C., 255° C. and 265° C. The benefits of this invention can be realized by operating at or above the minimum pressures shown in FIG. 1. In order to operate at lower pressures, a lower mole ratio reaction mixture must be used as will be apparent from FIG. 1.

For example, from FIG. 1 it will be seen that for secondary esterification at a mole ratio of 1.2:1 (EG/TA) and at a temperature of 255° C., the minimum possible operating pressure is about 330 Torr. Thus, when a reflux column is used, the feed to the secondary esterifier can be a 1.2/1 mole ratio feed and the reaction can be run at a temperature of 255° C. while the pressure can be maintained within the range between 330 Torr and 740 Torr with reflux ranging from 100 percent to 10–15 percent respectively. Pressure chosen within the above range will determine oligomer properties as discussed below.

Similarly, if vacuum or inert gas addition is used without a reflux condenser, in order to maintain a 1.2/1 mole ratio reaction mixture in the esterifier at a temperature of 255° C., pressure must be maintained above about 330 Torr and excess glycol (above 1.2/1) must be added to the esterifier, e.g., with the feed, to compensate for glycol lost in the overhead. The amount of excess glycol added will be dependent on the chosen pressure. In this regard operations near the limits shown in FIG. 1 will require substantial excess glycol addition and are not preferred as a practical matter when no reflux column is used. Preferably when no reflux column is used, pressure will be maintained at least about 30–40 Torr or greater above the limits shown in FIG. 1 depending on mole ratio. Thus with low mole ratio reaction mixtures, e.g., 1.05/1, operations to within 30–40 Torr of minimum pressure are practical whereas with higher mole ratios, e.g., 1.2/1, operations are best kept 80–100 Torr above minimum pressure.

Figure 2:
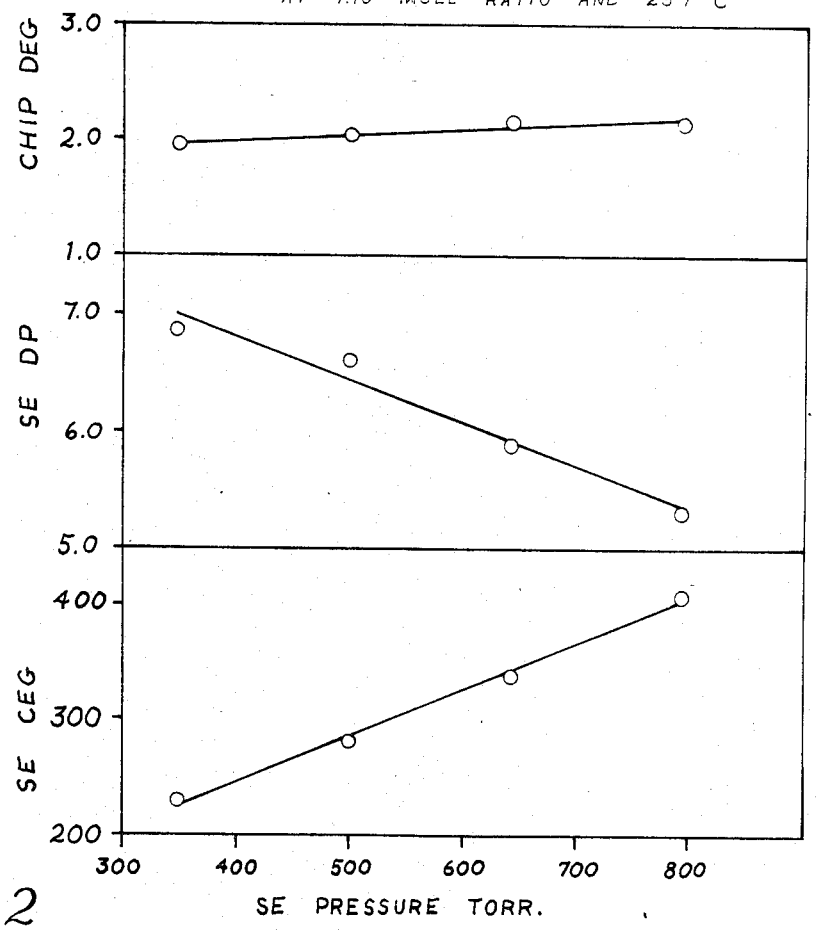

As indicated above, choice of sub-atmosphere operating pressure in the secondary esterifier will determine properties of the polyester oligomer produced. This is illustrated in FIG. 2 which graphically depicts the dependence on secondary esterifier pressure of oligomer properties of carboxyl end group (CEG); degree of polymerization (DP) and diethylene glycol content (DEG). Surprisingly, even though secondary esterification (SE) operating temperature and mole ratio of the reaction mixture are held constant, these can be varied simply by varying sub-atmospheric pressure in the secondary esterifier.

The oligomers prepared in the secondary esterification zone can be continuously removed from the secondary esterification zone and directly fed to polymerization reactors to form the ultimate fiber or film-forming polymer product. Greater vacuum is applied in a batch process. Polymerization of the oligomers is obtained by heating the oligomers at temperatures of about 270° to about 290° C. at sub-atmospheric pressures of about 0.5 to about 5 Torr and preferably about 1.0 to about 3.0 Torr typically in two or more stages of decreasing pressure to achieve the desired molecular weight, such conditions being well known to those skilled in the art.

The esterification reactions employed in the process of the present invention may be accomplished without the assistance of a catalyst and are accordingly free of metals or metallic compounds. In order to attain a high molecular weight polymer more quickly, a small amount, e.g., 0.02–0.10% by weight of an antimony compound such as antimony oxide can be incorporated in the reaction mixture as such compounds are comparatively innocuous towards polymer color and stability.

The following examples together with comparative test results shown in the accompanying Table illustrate the practice of the present invention. It should be understood, however, that the examples are illustrative and not exclusive.

EXAMPLES 1–4

There was admitted, to a feed vessel equipped with a stirrer and continuous metering devices, from separate supply sources, a mixture of ethylene glycol and terephthalic acid at a mole ratio of 1.2:1, whereby a suspension was prepared and pumped to a primary esterifier (PE) which consisted of a continuous stirred tank reactor wherein the ethylene glycol and terephthalic acid were reacted at 250° C. for 165 minutes, the pressure being maintained at 10 psig. Water formed in the primary esterification reaction was continuously distilled out via a reflux column. The glycol esters were continuously discharged from the PE reactor and passed to a secondary esterifier (SE) consisting of a second stirred tank reactor equipped with a vacuum operated distillation column provided with internal reflux means.

The glycol esters prepared in the PE were oligomerized at 250° C. and 6.8 psia pressure for 90 minutes in the secondary esterifier. Water formed during the secondary esterification reaction was continuously discharged and separated from the glycol in a distillation column which was maintained at a top temperature of 77° C. and a pressure of 6.0 psia. The glycol separated from the water was continuously recycled to the secondary esterifier. The oligomer formed in the secondary esterifier was continuously passed into a low polymerizer (LP) vessel which was also a continuous flow reactor with 80 minutes residence time. The LP temperature was 280° C. and the reactor was evacuated to a vacuum corresponding to 10 mm of mercury (Torr). The low molecular weight polymer flowed continuously to a high polymerizer (HP) reactor which was a horizontal vessel with agitator to expose polymer surface to the 1.0 Torr vacuum in the vessel maintained at 277° C. The polymerized product was withdrawn continuously from the high polymerizer and passed through an extrusion apparatus wherein the polymerized product was extruded in strand form and the solidified polymer was cut into chips. Upon examination, the polymer was shown to have an intrinsic viscosity of 0.654, a CEG content of 11.1 and a DEG content of 1.57.

The above procedure was repeated, the effect of glycol/acid mole ratio (MR), temperature, pressure and recycling of the ethylene glycol in the secondary esterification reaction being studied and the results obtained being summarized in Table 1 below.

For purposes of comparison, the procedure of the example was repeated in a series of runs with the exception that the secondary esterification reaction was carried out at atmospheric pressure and ethylene glycol was distilled out and not recycled to the secondary esterifier following the practice of the prior art. The results of these comparative runs designated by the symbol "C" are also shown in Table 1 below.

TABLE 1

| EX- | PE Conditions | | | SE Conditions | | |
|---|---|---|---|---|---|---|
| AM- | Feed | Press. | Temp. | Press. | Temp. | EG Removed* |
| PLE | MR | psig | °C. | psia | °C. | MR[1] |

TABLE 1-continued

| | | | | | | |
|---|---|---|---|---|---|---|
| 1. | 1.20 | 10 | 250 | 6.8 | 250 | None |
| 2. | 1.10 | 40 | 265 | 6.8 | 257 | None |
| 3. | 1.05 | 10 | 261 | 4.8 | 259 | None |
| 4. | 1.05 | 10 | 259 | 3.9 | 259 | 0.010 |
| $C_1$ | 1.20 | 10 | 250 | 15.3 | 265 | 0.020 |
| $C_2$ | 1.15 | 40 | 265 | 15.3 | 265 | 0.015 |
| $C_3$ | 1.10 | 10 | 257 | 15.3 | 265 | 0.006 |

| EX- | Oligomer Properties | | | Polymer Properties*** | | | |
|---|---|---|---|---|---|---|---|
| AMPLE | CEG | DEG | DP** | MR | CEG | DEG | IV |
| 1. | 101 | 1.18 | 5.6 | 1.20 | 11.1 | 1.57 | .654 |
| 2. | 227 | 1.74 | 6.9 | 1.10 | 17.9 | 1.96 | .561 |
| 3. | 309 | 1.05 | 8.8 | 1.05 | 20.0 | 1.25 | .776 |
| 4. | 304 | 1.01 | 9.6 | 1.04 | 21.0 | 1.19 | .796 |
| $C_1$ | 220 | 1.48 | 5.7 | 1.18 | 20.2 | 1.93 | .597 |
| $C_2$ | 430 | 1.89 | 5.8 | 1.14 | 35.1 | 2.28 | .604 |
| $C_3$ | 314 | 1.31 | 6.1 | 1.09 | 24.9 | 1.72 | .642 |

*Amount of ethylene glycol allowed to escape, and not recycled, expressed in mole ratio equivalents ($MR^1$).
**DP = number of glycol ester units in the oligomer.
***The polymerization of Example 2 was conducted at 2.3 Torr instead of 1.0 Torr LP conditions were 20 Torr pressure and 275° C. temp. The polymerizations of Examples 3 and 4 were conducted at 282° C. instead of 277° C.

The carboxyl end group (CEG) concentration was determined by dissolving a sample of the polyethylene terephthalate in heated O-Cresol and titrating with .1N NaOh to a potentiometric end point. the results are reported s microequivalents per gram of polymer ($\mu$eq/g).

The ethylene glycol dimer content (DEG) was determined by GC analysis and is reported as mole percent based on EG.

The intrinsic viscosity (IV) measurements were carried out in 8% solution in o-chlorophenol at 25° C. The measurement serves as a measure of the degree of polymerizatin, namely, the higher the IV, the higher the molecular weight and therefor the greater the degree of polymerization. In film and fiber applications, it is generally accepted that for polyethylene terephthalate, an IV in the range of 0.5-8.0 is preferred.

By reference to the Table, it is readily apparent that the polyethylene terephthalate compositions obtained by the process of the present invention (Run Nos. 1-4) are superior to polyethylene terephthalate compositions obtained using prior art conditions (Run Nos. $C_1$-$C_3$). Polyethylene terephthalate compositions are prepared having substantially lower CEG and DEG contents without sacrifice of oligomer DP especially when compared to polyethylene terephthalate prepared without sub-atmospheric esterification. (Example 4 demonstrates that a portion of the EG can be removed by the recycling of ethylene glycol to the secondary esterification reaction at sub-atmospheric pressure.) By further reference to the Table, it is further noted that the oligomers prepared in accordance with the present invention were polymerized to correspondingly low CEG and DEG content polymers having an IV suitable for fiber applications.

EXAMPLE 5

The procedure of Examples 1-4 is repeated except that the distillation column is removed from the secondary esterification vessel. The overheads consisting primarily of glycol and water are continuously removed and passed to a separate recovery unit for glycol recovery. The following results are obtained.

| PE Conditions | | | SE Conditions | | | Monomer Properties | | | |
|---|---|---|---|---|---|---|---|---|---|
| Feed MR | Press psig | Temp °C. | Press psia | Temp °C. | EG Removed $MR^1$ | CEG $\mu$ eq/g | DEG mole % | DP | MR |
| 1.20 | 40 | 260 | 4.8 | 259 | 0.15 | 310 | 1.76 | 9 | 1.05 |

It can be seen that results are obtained equivalent to operating with full reflux of glycol overheads using a 1.05 EG/TA mole ratio feed, but DEG is higher due to higher mole ratio in the PE.

EXAMPLES 6-9

The procedures of Example 5 are repeated except that nitrogen is added to the secondary esterifier at the rates shown below and the secondary esterifier is operated at atmospheric pressure. In these examples the primary esterifier is operated at a pressure of 40 psig and a temperature of 257° C. The secondary esterifier temperature is 257° C. and the nitrogen is heated to the same temperature to prevent condensation in the vapor space. In all four cases a 1.20 mole ratio feed is used and no other glycol is added to the system. The following results are obtained.

TABLE 3

| | Example | | | |
|---|---|---|---|---|
| | 6 | 7 | 8 | 9 |
| SE Mole Ratio | 1.17 | 1.11 | 1.09 | 1.05 |
| EG Removed, MR EQ | 0.03 | 0.09 | 0.11 | 0.15 |
| Oligomer CEG, eq/gm | 290 | 256 | 264 | 308 |
| Oligomer DP | 5.3 | 6.5 | 7.0 | 8.7 |
| Oligomer MP, °C. | 239 | 243 | 245 | 252 |
| Nitrogen Required, SCF/1000 lb Feed to SE | 0 | 295 | 535 | 923 |

EXAMPLES 10-13

The procedures of Examples 6-9 are repeated except that the EG/TA paste fed to the PE has a 1.15 mole ratio and the PE is operated at 25 psig and 257° C. The following results are obtained.

TABLE 4

| | Example | | | |
|---|---|---|---|---|
| | 10 | 11 | 12 | 13 |
| SE Mole Ratio | 1.13 | 1.11 | 1.09 | 1.05 |
| EG Removed, MR EQ | 0.02 | 0.04 | 0.06 | 0.10 |
| Oligomer CEG, eq/gm | 322 | 292 | 281 | 312 |
| Oligomer DP | 5.6 | 6.2 | 6.9 | 8.5 |
| Oligomer MP, °C. | 241 | 242 | 245 | 251 |
| Nitrogen Required, SCF/1000 lb Feed to SE | 19 | 113 | 225 | 600 |

The invention has been described in considerable detail with reference to specific embodiments thereof. But deviations and modifications can be effected within the spirit and scope of the invention as described in the foregoing specification and defined in the appended claims.

What is claimed is:

1. In the two-stage esterification reaction of a glycol and a dicarboxylic acid for the production of synthetic linear polyesters; the improvement which comprises introducing a glycol ester of a dicarboxylic acid feed into the second stage, said feed having an average degree of polymerization greater than 1 and a degree of esterification such that less than 30 mole percent of the acid end groups are unreacted, maintaining the sum of the partial vapor pressures of glycol and water in said second stage at less than 740 Torr, and maintaining a liquid glycol phase in said secondary esterification stage.

2. The process of claim 1 wherein said sum of the partial vapor pressures of glycol and water in said second stage is maintained at between about 100 and about 650 Torr.

3. The process of claim 1 wherein said sum of the partial vapor pressures of glycol and water in said second stage is maintained at between about 150 and about 450 Torr.

4. The process of claim 1 wherein said glycol is ethylene glycol and said dicarboxylic acid is terephthalic acid.

5. The process of claim 4 wherein said degree of esterification is such that less than 20 mole percent of the acid end groups are unreacted.

6. The process of claim 5 wherein the mole ratio of glycol to dicarboxylic acid is 1.2 or less.

7. The process of claim 1 wherein the water and glycol vapors released from said secondary esterification stage are passed to a distillation zone wherein glycol is condensed and at least a portion of said condensed glycol is returned to the secondary esterification stage.

8. The process of claim 1 wherein the sum of partial vapor pressures of glycol and water in said secondary esterification stage is reduced by injecting an inert gas into the vapor space within the secondary esterification zone.

9. The process of claim 1 wherein the amount of liquid glycol in said secondary esterification zone shall not exceed 20 mole percent based upon the acid, both reacted and unreacted.

10. The process of claim 1 wherein the amount of liquid glycol in the secondary esterification stage shall not exceed 5 mole percent based upon acid, both reacted and unreacted.

* * * * *